United States Patent [19]

Heimlich

[11] Patent Number: 4,987,895
[45] Date of Patent: Jan. 29, 1991

[54] TRACHEAL TUBE

[76] Inventor: Henry J. Heimlich, 17 Elmhurst Pl., Cincinnati, Ohio 45208

[21] Appl. No.: 209,880

[22] Filed: Jun. 22, 1988

Related U.S. Application Data

[63] Continuation-in-part of Ser. No. 915,699, Oct. 6, 1986, abandoned, which is a continuation-in-part of Ser. No. 715,384, Mar. 25, 1985, abandoned.

[51] Int. Cl.⁵ ............................................. A61M 16/00
[52] U.S. Cl. ............................. 128/207.14; 128/207.15; 104/161; 104/280
[58] Field of Search ..................... 128/200.26, 207.14, 128/207.18, 207.17; 604/96, 101, 280-284

[56] References Cited

U.S. PATENT DOCUMENTS

| | | | |
|---|---|---|---|
| 2,210,744 | 8/1940 | Winder . | |
| 2,599,521 | 6/1952 | Berman | 128/207.14 |
| 2,862,498 | 12/1958 | Weekes | 128/207.14 |
| 2,923,299 | 2/1960 | Blackwood | 128/207.17 |
| 3,034,510 | 5/1962 | Kittel | 604/101 |
| 3,388,705 | 6/1968 | Grosshandler | 128/207.14 |
| 3,443,564 | 5/1969 | Oehmig | 128/207.14 |
| 3,599,642 | 8/1971 | Tindel | 128/207.14 |
| 3,715,454 | 2/1973 | Kleykamp | 138/121 |
| 3,858,615 | 1/1975 | Wiegl | 128/204.18 |
| 3,908,704 | 9/1975 | Clement et al. | 138/121 |
| 3,948,274 | 4/1976 | Zeldman et al. | 128/207.14 |
| 4,056,104 | 11/1977 | Jasse | 128/207.15 |
| 4,063,561 | 12/1977 | DeSalvo | 128/207.15 |
| 4,067,331 | 1/1978 | Berman | 128/200.26 |
| 4,156,428 | 5/1979 | Henkin | 128/207.15 |
| 4,230,108 | 10/1980 | Young | 129/207.15 |
| 4,244,362 | 1/1981 | Anderson | 128/200.26 |
| 4,269,184 | 5/1981 | Montgomery | 128/207.14 |
| 4,275,724 | 6/1981 | Behrstock | 128/296.15 |
| 4,278,081 | 7/1981 | Jones | 128/207.15 |
| 4,280,500 | 7/1981 | Ono | 604/280 |
| 4,340,046 | 7/1982 | Cox | 128/207.17 |
| 4,363,323 | 12/1982 | Geiss | 128/207.18 |
| 4,471,776 | 9/1984 | Cor | 128/207.15 |
| 4,498,473 | 2/1985 | Geneg | 128/207.15 |
| 4,622,965 | 11/1986 | Teeple | 128/207.14 |

FOREIGN PATENT DOCUMENTS

| | | |
|---|---|---|
| 0216660 | 4/1987 | European Pat. Off. ....... 128/207.15 |
| 2140755 | 4/1981 | Fed. Rep. of Germany . |
| 1193670 | 8/1987 | Japan . |

Primary Examiner—Randall L. Green
Assistant Examiner—K. M. Reichle
Attorney, Agent, or Firm—Wood, Herron & Evans

[57] ABSTRACT

Disclosed herein is an improved tracheal tube which accommodates and follows the axial lengthening, shortening and translating movement of the trachea in actions such as breathing and swallowing, so as to minimize relative movement between the trachea and the tube where the tube inner end engages and bears against the trachea. In preferred form, the tube has two or more rigid, longitudinally spaced tubular support sections, including its inner end portion and an outer portion which are fixed in position with respect to the patient. The support sections support radially and connect at least one filmy tubular collapsible section between them. The collapsible section folds and unfolds on itself in the axial direction virtually without resistance, in response to movement of the trachea which tends to shorten or lengthen the distance between the support sections. The ability of the tracheal tube to easily extend and contract axially along with the trachea minimizes abrasions and ulcerations which could otherwise occur through rubbing of the tracheal tube against the trachea.

Also disclosed is a tracheal tube having a flat back wall which is disposed to be positioned against the posterior wall of the trachea. This reduces local indenting pressure on the trachea which otherwise could tend to push into the esophagus.

8 Claims, 2 Drawing Sheets

RESTING  SWALLOWING

RESTING  SWALLOWING

TRACHEAL TUBE

RELATED APPLICATION

This application is a continuation-in-part of my copending application Ser. No. 915,699, filed Oct. 6, 1986, now abandoned, which was in turn a continuation-in-part of application Ser. No. 715,384, filed Mar. 25, 1985, now abandoned.

FIELD OF THE INVENTION

This invention relates generally to tracheal tubes, such as tracheostomy and endotracheal tubes.

BACKGROUND OF THE INVENTION

Tracheal tubes are used in conjunction with breathing problems to provide a better airway in the neck of a patient requiring assistance in breathing, as well as for conduction of anesthetic gas during a surgical operation. Tracheal tubes are of two general types, namely, tracheostomy tubes and endotracheal tubes.

A tracheostomy tube is inserted into the trachea of the patient through a surgically produced opening in the anterior neck. The shape of the tracheostomy tube is angled or L-shaped so that its upper end protrudes generally perpendicularly from the neck while its distal portion extends downwardly inside and parallel to the trachea. An endotracheal tube is inserted into the trachea through the mouth or nose, and is usually formed without a sharp bend but otherwise is substantially similar to the tracheostomy tube.

In a tracheal tube which is to serve as a conduit for anesthetic gas or to support breathing by providing a flow of oxygen or air from a respiration device, an inflatable balloon or cuff is ordinarily mounted adjacent the distal (inner) end of the tube. When the cuff is expanded by filling it with air, it presses against the tracheal wall thereby occluding the annular space between the tube and the wall. As a result, air flowing through the tube will fill the lungs without escaping back around the outside of the tube, because the cuff occludes that passage. Subsequent release of air pressure allows the lungs to exhale through the tube as in normal respiration.

Problems associated with present tracheal tubes detract from their utility, particularly where long term use of the tube is required or desirable, e.g., for more than seven days of intubation. One very significant problem is that they tend to cause abrasions and ulcerations; these result when the cuff and/or inner end of the tube rubs or scrapes against the tracheal wall. For example, in respiration each inhalation draws the trachea downwardly relative to the cuff, the trachea then returning upwardly in exhalation. In addition, the trachea increases and decreases in length as the tracheal rings move apart and come together. Normally, there may be about 18 such respirations a minute so that relative movement —and hence abrasion—is frequent. In addition, with each swallow the trachea moves upwardly (relative to the cuff) by elevation of the larynx; the trachea rapidly descends upon conclusion of the swallow. The swallowing movements occur at short intervals voluntarily or spontaneously to empty the pharynx of saliva, as well as during the ingestion of food. Such respiratory and swallowing movements, as well as sneezing, sighing and coughing, cause prior art tracheal tubes, which are fixed in place at their upper end and are of fixed length, to move up and down in relation to the trachea. This causes the inner end of the tube to scrape against the wall of the trachea, resulting in erosion of the posterior wall of the trachea and even of the adjacent esophagus. Movement of the inflatable cuff of the tube likewise results in rubbing and erosion of the mucosa of the trachea, causing abrasions and ulcerations to result. Ultimately scar tissue can build up, which can hinder breathing after tube removal.

The complications associated with prolonged intubation can be particularly severe. For example, chronic laryngotracheal stenoses can result, which may require a permanent tracheostomy, as well as tracheomalacia, the formation of fistulae between the trachea and the esophagus, and erosion of the anterior trachea and the innominate artery.

THE PRIOR ART

Prior attempts have been made to overcome the problem of abrasion and ulceration caused by movements of the tube in relation to the trachea, but have all fallen short of solving the problem. For example, tracheal tubes have been made flexible, rather than the traditional rigid type. U.S. Pat. Nos. 2,923,299; 3,599,642; 3,948,274; 4,269,184; 4,275,724; 4,278,081; 4,430,046; and 4,498,473 are exemplary of various types of flexible or corrugated unitary tracheostomy tubes. The flexibility so provided permits the tubes to follow lateral movements of the head and neck without significant resistance to those movements, and to adapt to the contour of the neck and trachea. This serves to prevent the end of the tube from scraping the tracheal wall as severely as a more rigid tracheal tube does. The '046 tracheostomy tube is also said to be capable of conforming to any depth of the trachea within the neck, to accommodate differences in patient neck length. The U.S. Pat. No. 4,278,081 shows a flexible tube with a cuff at the inner end and a tube supported by spiral wire for better flexibility. One Pat. No. 4,280,500, shows a catheter tube which has porous radial sections, but the tube is stated to have the appropriate degree of stiffness to insure smooth insertion into a vein, together with the necessary flexibility to allow it to advance along tortuous vessels without impairing the walls.

None of the prior art, however, address the problem of accommodating changes in the axial length of the trachea caused by respiration and swallowing which result in the distal portion of the tracheal tube moving relative to the trachea, with resulting abrasion and ulceration of the trachea. The U.S. Pat. No. 4,340,046 refers to its corrugated tracheostomy tube as absorbing and cushioning thrust created by the pulsations of a mechanical respirator to eliminate abrasive motion of the tracheostomy tube. However, that structure does not eliminate motion within the neck relative to the cuff. The corrugations abut or rest on top of one another, so that within the trachea the tube cannot shorten axially in response to tracheal movement Moreover, the tube of that patent is unitary and the material is relatively rigid in order to keep the tube open. Its structure thus does not enable the intratracheal portion of the tube to shorten and lengthen, and thereby avoid abrasion, in response to shortening, lengthening, and upward and downward motion of the trachea with every breath, swallow, sneeze, sigh or cough.

Another problem arises with tracheostomy tubes which have a generally constant tube radius, i.e., where the tube is generally of a constant circular axial cross-section. Regardless of flexibility, the tube impinges upon the posterior wall of the trachea and anterior wall of the esophagus, indenting the latter into the esophageal lumen and thereby partially blocking the esophagus. As a result, patients with tracheostomy tubes often have difficulty swallowing food, and frequently aspirate food particles into the trachea, which can in turn develop into aspiration pneumonia.

It is therefore an objective of the present invention to provide an improved tracheal tube which is capable of free axial extension and contraction to allow the tube to move along with upward and downward motions of the trachea, such as from respiration and swallowing, and to prevent, or at least significantly reduce, rubbing of the tube against the tracheal wall.

Another objective of the present invention is to provide an improved tracheal tube which does not block the esophagus and thereby interfere with food swallowing.

SUMMARY OF THE INVENTION

The present invention is an improved tracheal tube which readily "collapses" or shortens axially as the trachea shortens, without causing friction or abrasion of the inner end portion of the tube upon the trachea. In this tube, the outer and inner end portions are rigid, and axial shortening and lengthening between them is obtained by providing at least one axially collapsible section connected between them, so that all shortening and lengthening of the tube due to movement of the trachea takes place in the collapsible section. Unlike tubes incorporating a spiral wire which, like a spring, tends to resist changes in length of the tube, the collapsible section of the present tube collapses more readily than the inner end or outer portions can move relative to the positions at which they engage the patient. In other words, essentially all lengthening and shortening of the tube is accommodated by axial folding of the collapsible section, and essentially no movement relative to the trachea takes place at the inner end portion of the tube.

In a modified embodiment of the invention, the collapsible section, or a plurality of them, are supported against radial (but not axial) collapse by one or more axially spaced ring, C-shaped or cylindrical sections which are located inside of or around collapsible sections at axially spaced intervals, or which connect short axial segments of collapsible material. The ring-shaped sections circumferentially support the collapsible sections, with each ring being separated axially from an adjacent ring by a collapsible section. The collapsible section is so flaccid that, when the outer portion of the tube is fixed in place on the patient and the inner or distal end portion is fixed in the trachea as by an inflatable cuff, the tube can easily shorten by folding of the collapsible section upon itself, between the support sections. Consequently, axial dimension changes to accommodate swallowing and so on take place between the ends of the tube, rather than by movement of the tube inner end relative to the adjacent part of the trachea. The frictional forces (that is, the resistance to movement) of the ends of the tube as they bear on the patient are far greater than the small force required to shorten or extend the collapsible section, so that no relative movement occurs at the tube inner end which otherwise could lead to abrasion or formation of scar tissue. Thus, as that portion of the trachea which is in contact with the cuff descends, the collapsed section of the tube extends; and as that portion of the trachea ascends, the rigid support sections approach one another as the collapsible section shortens or folds.

The shape of the tube may be similar to the shape of the trachea itself. In the trachea, a series of cartilaginous semi-rigid rings maintain the diameter of the airway. Each ring of the trachea is separated from those above and below it by thin, soft tissue. Each cartilaginous ring is therefore capable of axial movement toward or away from an adjacent ring, enabling the trachea to extend or contract in length. Although the relative movement between any two cartilaginous rings may be small, the sum of the movements between all of the rings allows for considerable changes in length. The tracheal tube of this invention may follow the same principle. Moreover, when the trachea is at its minimum or maximum length, the trachea can move as a whole. This invention can also accommodate such axial translating movement of the trachea as a whole, without abrasion.

The tube of this invention is made of two different materials; the collapsible section is a soft, flexible, easily collapsible material, like a plastic film; while the outer and inner end portions and any ring-shaped members are made of a material which is sufficiently rigid as not to distend or collapse in use. The collapsible material is flaccid to allow free axial movement between rigid portions of the tube; the rigid portions maintain an open passage through it, and are not required to distend. The collapsible section could in fact collapse radially if not supported. This separation of functions minimizes any resistance to axial movement so that the cuff moves synchronously with even slight axial movement of the trachea. This construction also permits the tube to move in a lateral direction to conform to the contour of the patient's airway and neck, and to follow the motions of the neck and head.

In a second aspect of the present invention, a tracheal tube is provided which has a flat backwall area that fits against the posterior wall of the trachea. This eliminates the interference with normal deglutition, i.e., food swallowing, such as is caused by prior art tubes of circular shape which indent the esophageal wall. The flat tube wall can itself be of collapsible material, to conform to axial movement as described; or it can be of rigid material similar to the rings. A flexible posterior wall along the full length of the tube, enables greater flexibility of the tube in all directions. While the cuff can fully encircle the tube, in another modified form the cuff only partially encircles the tube and does not overlie the flat sidewall. This eliminates point or line pressure of the cuff on the posterior wall of the trachea and thereby further reduces any interference with the normal swallowing action of the patient.

A rigid or malleable internal obturator or stent is used to push the tube into the trachea, the stent being removed after insertion. Where desired, an inner cannula can also be inserted into the tracheal tube. This cannula can be loosely fitted, or provided with a design similar to that of the improved tracheal tube to further prevent any restriction on the axial movement of the tracheal tube.

The foregoing objectives, features and advantages of the present invention will be more readily understood upon consideration of the following detailed description of the invention taken in conjunction with the accompanying drawings, in which:

DETAILED DESCRIPTION OF THE INVENTION

Figure 1:
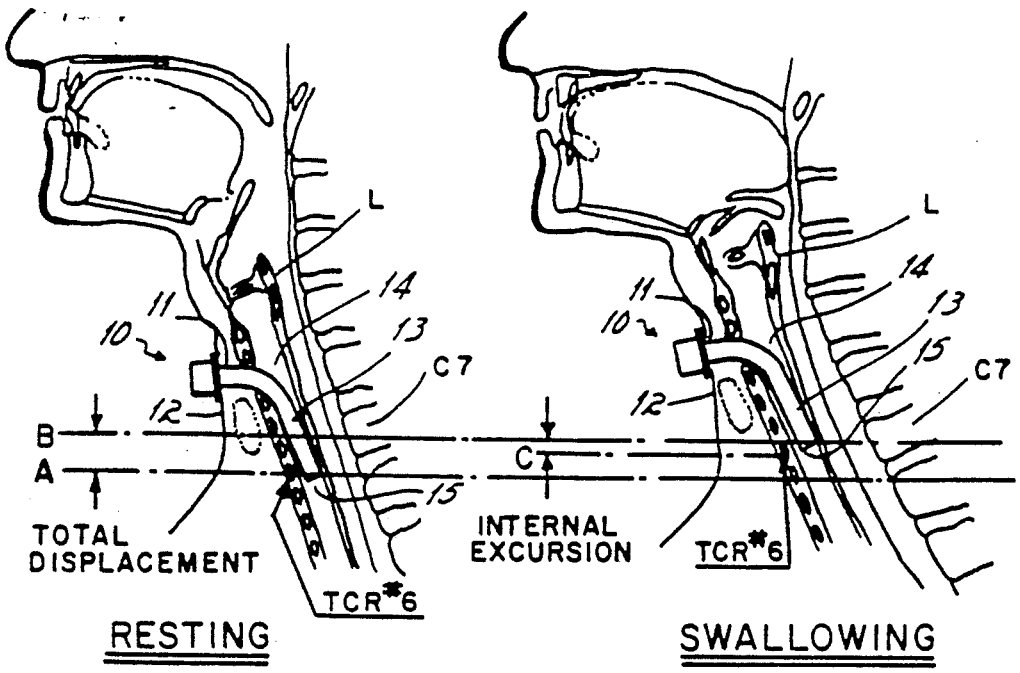
FIG. 1 is two partial longitudinal sections, schematic in form, of a patient's neck in which a prior art tracheostomy tube is inserted, showing on the left side the tube in its position in the trachea during a rest (i.e., non-swallowing) period, and on the right side showing the tube in its position during swallowing.

FIG. 1 serves to illustrate the problem presented by a prior art tracheal tube, arising from its movement relative to the trachea, resulting in injury to the tracheal wall. A prior art tracheostomy tube 10 is shown inserted through a hole 11 in the patient's neck 12, with the distal portion 13 of the tracheal tube 10 extending downwardly into the trachea 14. The left hand illustration in FIG. 1 shows the prior art tracheal tube 10 in a resting position. The distal portion 13 terminates in an end 15 which is shown contacting the posterior wall of the trachea 14 at the level of line A. As shown herein, the end of the tube 15 is at the level of the tracheal cartilaginous ring, indicated at TCR6, and also in the vicinity of vertebra C7, which is stationary relative to TCR6.

The right hand illustration shows tracheal tube 10 after initiation of a swallowing action. As the larynx L moves upwardly, the upper end of the trachea and the tracheostomy tube 10 also move upwardly This causes the end of the tube 15 to move up to a position indicated by the line B, corresponding to a total displacement (relative to the vertebra C7) corresponding to the distance B-A. The resulting internal excursion of the end of the tube 15 is indicated by the distance B-C, representing the travel of the tube end 15 in relation to TCR6. This internal excursion is typically of the order of about one cm.

As the tube end 15 moves upwardly in relation to TCR6, it rubs against the tracheal wall. Movement of the tube end 15 downwardly following swallowing (returning to the rest position) causes further rubbing and scraping of the posterior tracheal wall. A balloon or inflatable cuff attached to the distal portion 13 of the tracheostomy tube 10 could increase the area and extent of injury through constant rubbing of the cuff against the wall of the trachea from tube movement. As previously indicated, this rubbing and scraping results in abrasions and ulcerations leading to damage of the trachea mucosa, ulcerations, scarring and increased risk of tracheal necrosis.

Figure 3:
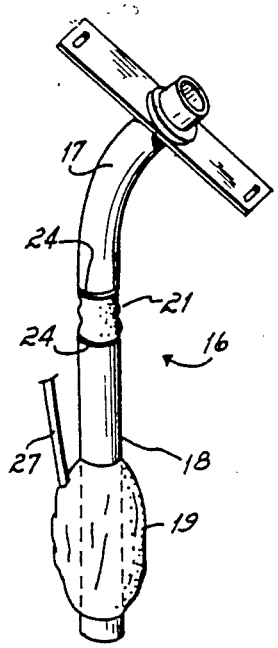
FIG. 3 is a perspective view of a preferred form of tracheostomy tube in accordance with the principles of this invention.

With reference to FIG. 3, the presently preferred embodiment of this invention is shown in the form of an tracheostomy tube 16 having a rigid (not collapsible) outer portion 17 and a rigid inner end portion 18 which may have an inflatable cuff or balloon 19 around it, or other means to secure the inner end in the trachea. Cuff 19 may be of any suitable type known in the art. It is inflated after the tube has been inserted into the trachea of the patient to fix the distal portion at a desired point within the trachea. The cuff 19 is inflated by passing air down an inflating tube 27 until the air fills out the cuff and seals it against the inside surface of the trachea. The inflation tube 27 communicates with a suitable inflation mechanism, well known to those of ordinary skill in the art, and ordinarily includes a balloon-like reservoir (not shown) to indicate the inflation of cuff 19. (Inflation tube 27 does not structurally connect the rigid sections.) The rigidity of inner end portion 18 prevents cuff 19 from collapsing or restricting the interior channel of the tube upon inflation of the cuff. The patient can also breathe directly through the tube 16, when a mechanical respirator is not necessary.

Figure 5:
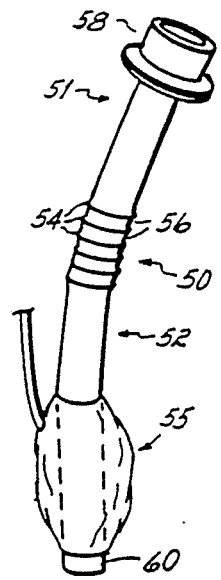
FIG. 5 is a foreshortened perspective view of an endotracheal tube in accordance with another embodiment of the invention, wherein the collapsible section is supported by a short series of rings, all located in the mid-portion of the tube, between rigid end portions, the outer portion being shown straight for purposes of illustration.
Figure 6:
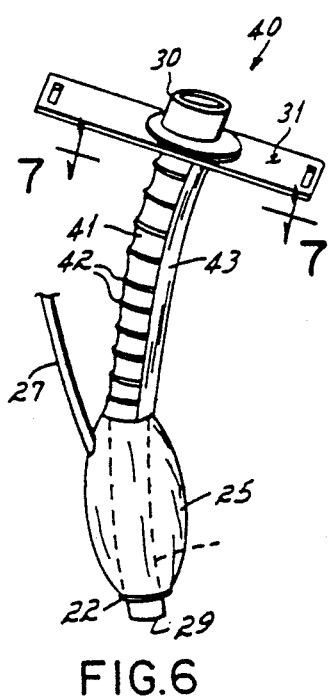
FIG. 6 is a perspective view of another embodiment of a tracheostomy tube in accordance with the invention, having a flat backwall.

Between the rigid portions 17 and 18 is a collapsible section 21 which is formed of a thin, soft, filmy, flexible, tubular material such as silicone rubber, polyurethane, polyethylene or polyethylene terephthalate. It is connected at annular areas 24, 24 at its ends to the rigid sections 17 and 18. The rigid sections comprise support sections for the collapsible section which otherwise would collapse radially. The length of the collapsible section 21 need only be sufficient to accommodate the change of tracheal length that accompanies swallowing and breathing; typically about ½-¾" may be sufficient. The length of the collapsible section, in relation to its diameter, should not be so great that it can collapse radially to the point of closing the air passage within it. The smaller the diameter of the collapsible section, the shorter it must be, in order to avoid radial restriction, unless the collapsible section is supported along its length by additional support means as shown in the embodiments of FIGS. 4, 5 and 6.

Figure 2:
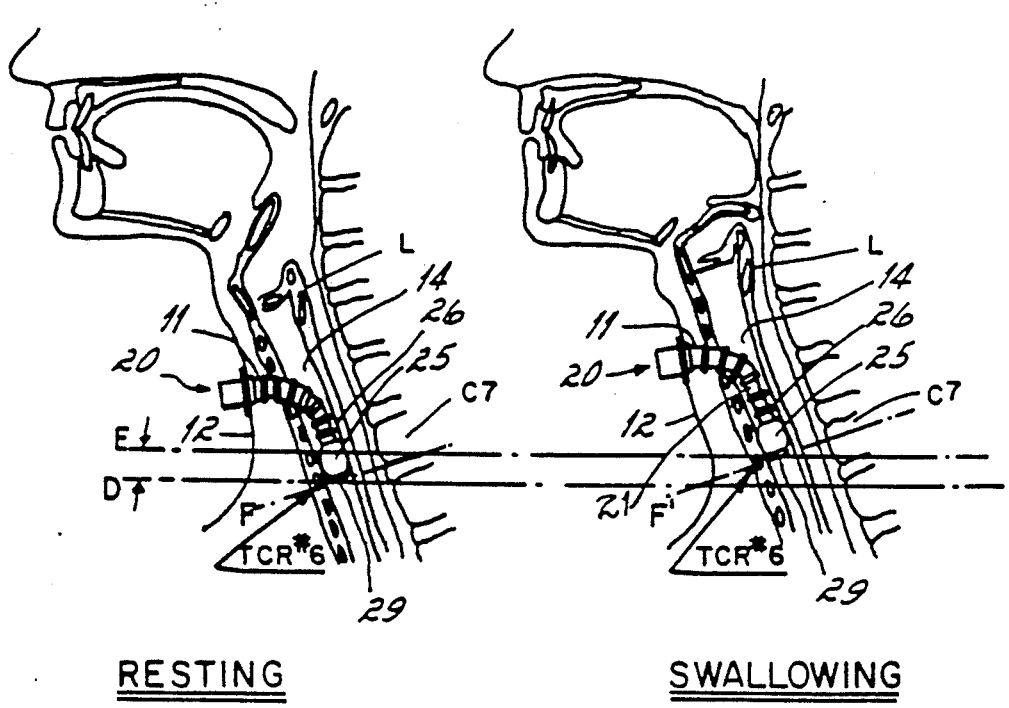
FIG. 2 is a comparative sectional view similar to FIG. 1, showing an improved tracheal tube made in accordance with the principles of this invention, showing on the left the tube in a resting position within the trachea, and on the right in its position during swallowing.
Figure 4:
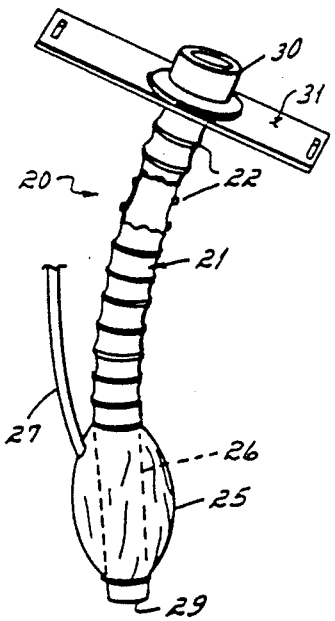
FIG. 4 is a perspective view of a tracheostomy tube in accordance with a modified embodiment of the invention, wherein the collapsible section of the tube is much longer and is supported radially but not axially along its length by a series of rings.

FIG. 4 of the drawings shows a tracheostomy tube 20 in accordance with a modified form of the invention, wherein the collapsible section 21 of the tube is relatively long and is supported radially by a plurality of semi-rigid rings 22 which maintain an adequate internal passage through the collapsible segments to provide a conduit through which gas can pass. The rings 22 may be of a semi-rigid plastic material; their number, dimensions, and spacing are not critical so long as they provide adequate radial support for the collapsible section 21. The rings can have a cylindrical internal and/or external surface, or can be round, oval, flat with rounded edges, or a combination of these shapes. The rings 22 may be fixed to either the interior or exterior of a continuous tubular collapsible section, so that the collapsible section is presented between the rings; or they can be embedded within the wall of a thickened portion of the collapsible material. As shown in the embodiment of FIG. 4, the rings 22 are substantially coaxial with the longitudinal axis of the collapsible section 21 A conventional collar or taping flange 31 is provided on a fitting 30 to position the outer end of tube 20 adjacent the opening formed in the patient's neck (FIG. 2). In use this collar is secured to the patient's neck, for example by encircling umbilical tape, so that the outer end of the tube does not move axially relative to the patient and the tube does not come out of the opening.

With specific reference to FIG. 2, a tracheostomy tube 20 in accordance with the FIG. 4 embodiment just described is shown inserted through a hole 11 in the neck 12 of a patient. The tube outer portion is secured to the patient in known manner, as by umbilical tape encircling the neck as a necklace, passing through openings in the winged flange 31. (An endotracheal tube is also fixed in place externally by adhesive tape encircling it and fixed to the skin.) The cuff 25 is inflated to secure the rigid distal portion 26 of the tube in trachea 14, at about the level of the tracheal cartilaginous ring TCR6. It will be noted that the distal portion 26 is located in such a manner that the tube is not fully extended, that is, the collapsible section is slightly folded or collapsed between the rigid ends and between the rings. This permits the tube to extend axially. This is illustrated in the resting position of the tube shown in the left hand drawing of FIG. 2.

The right hand illustration in FIG. 2 shows the position of the tube upon initiation of the swallowing action by the patient. As the larynx L moves upwardly, the upper end of the trachea and the tube also move upwardly with the trachea. The total displacement of the tube, relative to a fixed point such as vertebra C7, is illustrated by the distance between lines D and E. The collapsible section 21 lengthens axially in synchronism with the axial movement of the trachea, i.e., the collapsible section unfolds and increases the length of the tube (see also FIG. 4). The inner end 26 thus remains in place within the trachea. This is shown by lines F and F', which respectively indicate the position of distal end 29 of the tube in relation to TCR6 in the resting and then in the swallowing position. As shown, there is no relative movement of the distal end 29. Since the cuff 25 remains stationary relative to the trachea 14, the cuff does not rub against the tracheal wall. There is thus no irritation, abrasion or ulceration of the tracheal wall. The inner end portion 26 of the tube would likewise remain in position upon conclusion of the swallowing action when the trachea and tube are returned to the resting position (indicated by line D).

The tube functions in the same manner when the trachea is drawn downward at the time of inhalation, and then moves upwardly on exhalation, whether respiration is spontaneous or induced by a mechanical respirator. Also, although a tracheostomy tube is specifically described in relation to FIGS. 4 and 6, it will be recognized that an endotracheal tube (FIG. 5) in accordance with the invention, inserted through the mouth or nose, operates in the same manner.

As shown in FIG. 5, the collapsible section 50 may be a portion of the tube which is supported by only a few supporting rings 54, between a rigid outer portion 51 and inner end portion 52. Again, a cuff 55 surrounds the rigid inner end portion 52, just above tube end 60. The tube shown in this embodiment is an endotracheal tube and has an outer end fixture 58, to be positioned adjacent the patient's mouth or nose.

Figure 7:
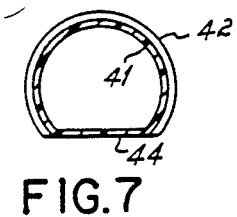
FIG. 7 is a cross-sectional view taken along line 7—7 of FIG. 6.

FIG. 6 illustrates a related aspect of this invention. The modified tracheostomy tube 40 has a collapsible section 41 between a rigid outer portion 30 and inner end portion 26, where the collapsible section is supported by a plurality of spaced C-shaped semi-rigid rings 42 along its length. As shown in FIGS. 6 and 7, each C-shaped semi-rigid ring 42 has a gap 44, across which the collapsible material extends. The C-shaped rings 42 are aligned with the ring gaps all on the same side, so that a soft flat backwall or stripe 43 is provided along a portion of tube 40. After insertion, this soft flat backwall 43 will be against the soft posterior wall of the trachea, thus preventing the tube from indenting the posterior wall of the trachea into the esophagus. (This flat backwall construction can also be used advantageously in rigid tubes having no collapsible section, as well as in tubes with a collapsible section and rigid supporting sections.) This feature eliminates, or substantially reduces, the difficulty which many patients have had in swallowing food caused by existing tracheostomy tubes of a relatively constant radius, because the tube does not exert an indenting line of force on the esophagus, which is in direct apposition to the posterior wall of the trachea.

The remainder of the construction of the modified embodiment of tube 40 may be the same as that of the previously described embodiment of the tube 20, and like numbers indicate identical parts and elements in both embodiments.

Figure 8:
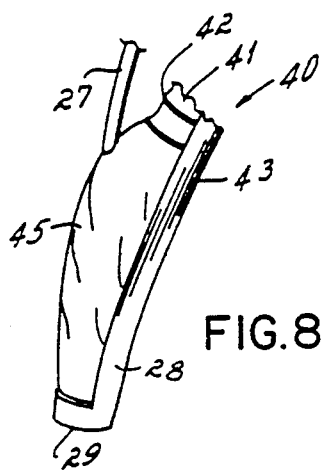
FIG. 8 shows a modified inflatable cuff for particular use with the embodiment of FIGS. 6 and 7.

FIG. 8 shows a modified inflatable cuff 45 for use with the modified tube 40 having the soft sidewall 43. The modified inflatable cuff 45 does not extend over the soft backwall 43, but instead only overlies the C-shaped supporting rings 42, which in this version of the invention, are provided along most of the length of the tube. This eliminates point pressure of the inflatable cuff 45 on the posterior wall of the trachea, to further reduce any interference with the normal swallowing action of the patient. Alternatively, the flat portion of the tube in the cuff can be rigid as at 28 in FIG. 8. The modified cuff of FIG. 8 provides the same advantages when used with a tube of round circumference. The cuff can be flat on the back, regardless of whether the tube is round or has a flat backwall.

Where supporting rings 22, 42 or 54 are used, it will be appreciated that they can be of different cross sections. The shape of the rings is not critical; instead of an oval or rounded sectional axial section, the rings can, for example, have a cylindrical section, be rectangular in axial section; offset or Z-shaped; and they can be thicker than the collapsible section to which or in which they are secured. The collapsible section itself need not be continuous; it can be formed in individual lengths, connected to and between the rings.

As seen in the embodiment of FIG. 5, the spacing between the rings 54 can be about ¼", by way of example and not limitation. Thus a tube having, say, six such rings, between seven collapsible portions 56, would permit the length of the tube between its rigid ends 51 and 52 to change up to about 1¾". This is more than sufficient to accommodate the usual tracheal movement.

Thus, while the invention has been described in connection with certain presently preferred embodiments, those skilled in the art will recognize modifications of structure, arrangement, portions, elements, materials and components which can be used in the practice of the invention without departing from the principles of this invention.

What is claimed is:

1. A tracheal tube comprising at least two tubular longitudinally spaced support sections which are sufficiently rigid to resist collapse in the radial direction in use,
    a tubular collapsible section joining and extending between the respective support sections, said collapsible section being made of pliant foldable material which is easily collapsible and re-extendable in use in its axial direction, said collapsible section adapted to collapse and re-extend axially in response to movement of the trachea in a direction which tends to shorten and extend said tube,
    the support sections being connected to one another only through the collapsible section and providing radial support for the collapsible section where the latter joins the support sections,
    said tube having an inner end portion which in use engages and bears against the trachea of a patient, and an outer portion which in use extends externally of the patient,
    means for securing said outer portion in fixed position externally of the patient,
    the axial collapsibility of the collapsible section between said support sections being such that it is adapted to fold and unfold between the support sections as the inner end portion of the tube moves with the trachea more easily than the outer portion and inner end portion of the tube can move relative to the positions at which they engage the patient,
    said tube thereby shortening and lengthening so that any change in the axial distance between said outer portion and said inner end portion is accommodated by folding or unfolding of the collapsible section and essentially no movement relative to the trachea occurs where the inner end portion of the tube engages and bears against the trachea.

2. The tracheal tube of claim 1 wherein one of said support sections provides said inner end portion and another of said support sections provides said outer portion.

3. The tracheal tube of claim 1 wherein said collapsible section is formed of flexible film material.

4. The tracheal tube of claim 1 further including means for securing said inner end portion within the trachea.

5. The tracheal tube of claim 4 wherein said means for securing said inner end portion within the trachea is an inflatable cuff around said inner end portion.

6. The tracheal tube of claim 1 further wherein said tube has a plurality of collapsible sections between said inner end portion and said outer portion, said collapsible sections being connected serially through rigid annular support sections which provide radial support of the collapsible sections and provide an internal passage for the passage of gas, and prevent said collapsible sections from collapsing radially and thereby constricting said passage.

7. The tracheal tube of claim 1 wherein said collapsible section is further supported by at least one discrete, relative rigid, planar, radial support ring, said ring positioned in said collapsible section and spaced between said inner end portion and said outer portion and providing radial support for said collapsible section to provide a passage therethrough for the passage of gas, and being connected only to said collapsible section.

8. The tracheal tube of claim 1 wherein said collapsible section is further supported by at lest one rigid discrete ringlike support member, said support member positioned in and connected to said collapsible section and spaced between said inner end portion and said outer portion said ringlike support member connected to said portions only by said collapsible section.

* * * * *